United States Patent [19]

Imai

[11] 4,207,260
[45] Jun. 10, 1980

[54] PREPARATION OF TERTIARY AMINES

[75] Inventor: Tamotsu Imai, Mt. Prospect, Ill.

[73] Assignee: UOP Inc., Des Plaines, Ill.

[21] Appl. No.: 971,283

[22] Filed: Dec. 20, 1978

[51] Int. Cl.$^2$ ............................................. C07C 85/08
[52] U.S. Cl. .................................. 260/577; 260/563 R;
260/563 C; 260/570.8 R; 260/570.9; 260/576;
260/583 R
[58] Field of Search .................... 260/563 R, 576, 577,
260/583 R, 585 C, 570.8 R, 570.9

[56] References Cited

U.S. PATENT DOCUMENTS

| | | | |
|---|---|---|---|
| 1,966,478 | 7/1934 | Baur | 260/585 C X |
| 2,219,879 | 10/1940 | Vanderbilt | 260/583 R |
| 2,452,602 | 11/1948 | Robinson et al. | 260/583 R |
| 2,477,943 | 8/1949 | Robinson et al. | 260/584 R |
| 3,091,641 | 5/1963 | Sweeney | 260/583 R |
| 3,336,386 | 8/1967 | Dovell et al. | 260/576 |
| 3,597,438 | 8/1971 | Blake | 260/585 C X |
| 3,658,824 | 4/1972 | Thoma et al. | 260/585 C X |
| 3,758,586 | 9/1973 | Coulson | 260/570.9 |
| 3,864,382 | 2/1975 | Funten et al. | 260/585 C X |

OTHER PUBLICATIONS

Ginsburg, "Concerning Amines", pp. 33–38, (1967).

*Primary Examiner*—John Doll
*Attorney, Agent, or Firm*—James R. Hoatson, Jr.; Raymond H. Nelson; William H. Page, II

[57] ABSTRACT

Tertiary amines may be prepared by reacting an aldehyde, hydrogen and a nitrogen-containing compound such as ammonia, a primary amine or a secondary amine in the presence of a rhodium- or ruthenium-containing catalyst at temperatures in the range of from about 50° to about 350° C. and a pressure in the range of from about 10 to about 300 atmospheres.

12 Claims, No Drawings

PREPARATION OF TERTIARY AMINES

BACKGROUND OF THE INVENTION

Heretofore tertiary amines have been prepared in a wide variety of reactions utilizing various metal-containing compounds as catalysts. For example, U.S. Pat. No. 3,091,641 discloses a process for preparing tertiary amines in which a secondary amine and an aliphatic ketone are reacted with carbon monoxide and water in the presence of an iron carbonyl catalyst such as iron pentacarbonyl or biscyclopentadienyl diiron tetracarbonyl. Another U.S. Patent, namely, U.S. Pat. No. 2,497,310 discloses the synthesis of amines in which an unsaturated compound, carbon monoxide, hydrogen and ammonia or a substitute ammonia are reacted in the presence of a cobalt catalyst although other catalysts which possess hydrogenation properties such as nickel, ruthenium, iron and copper may also be used. Another prior art reference, namely U.S. Pat. No. 3,947,458 is drawn to a process for preparing amines in which nitrogen-containing compounds and an olefin along with carbon monoxide and water are reacted in the presence of a catalyst comprising iron pentacarbonyl and a rhodium compound. In like manner, U.S. Pat. No. 3,234,283 also discloses a process for the preparation of trialkyl amines in which an olefin is reacted with carbon monoxide, hydrogen and a dialkyl amine in the presence of a catalyst consisting essentially of cobalt carbonyl trihydrocarbonphosphene. The hydrocarbon content of the catalyst is limited to trihydrocarbons containing a total of up to about 30 carbon atoms, the number of carbon atoms in any one of said hydrocarbon radicals not exceeding 18. Other prior art patents include U.S. Pat. No. 3,758,586 in which ethylene is reacted with secondary aliphatic amines in the presence of rhodium or iridium catalysts to form a tertiary amine in which one of the substituents is, of necessity, ethylene; U.S. Pat. No. 3,513,200 in which the preparation of tertiary amines is accomplished by reacting a secondary amine containing from 2 to about 20 carbon atoms with an aliphatic hydrocarbon olefin containing from about 2 to about 20 carbon atoms, as well as carbon monoxide and hydrogen in the presence of a complex catalyst comprising a Group VIII noble metal hydride in complex with a biphyllic ligand, said ligand containing phosphoric, arsenic or antimony; U.S. Pat. No. 3,412,158 which is drawn to a process for the preparation of aliphatic amines from the reaction of lower molecular weight olefins and ammonia, the primary product comprising a primary amine rather than a tertiary amine; U.S. Pat. No. 2,501,509 which is drawn to the preparation of amines by heating an ammonia type compound with a hydrocarbon olefinic compound utilizing an alkali metal catalyst such as sodium, this reference requires the presence of an organic liquid diluent for the olefinic reactant; and U.S. Pat. No. 2,422,631 in which aliphatic amines are produced by reacting an olefin, an oxide of carbon, hydrogen and an aminating agent in the presence of a hydrogenation-dehydration catalyst, examples of these catalysts being zinc chromate, zinc tungstate, chromium phosphate, cobalt oxide, iron oxide, etc.

In contradistinction to the above reactions, it will be hereinafter shown in greater detail that tertiary amines may be synthesized by utilizing a particular rhodium- or ruthenium-containing catalyst to obtain an economically attractive conversion of the olefin compound with an economically attractive selectivity to the desired product.

SPECIFICATION

This invention relates to a process for the synthesis of tertiary amines. More specifically, the invention is concerned with a process for synthesizing tertiary amines by reacting an aldehyde, hydrogen and a nitrogen-containing compound in the presence of certain catalytic compositions of matter to obtain the desired product.

Tertiary amines will find a wide variety of uses in the chemical field. For example, these compounds may be used in agricultural applications, acting as an inert surfactant for herbicides; for use in corrosion inhibition and crude oil pipelines; in cosmetic formulation; leather processing; paint formulation; secondary oil recovery; mineral separation (cationic flocculation or flotation), etc. A specific compound, namely, tributylamine is used as a solvent, as an intermediate in the preparation of other chemicals and as an inhibitor in hydraulic fluids. In view of these important chemical uses, it is therefore necessary to effect the preparation of the tertiary amines in an economically feasible manner, said process requiring a relatively quantitative conversion of the olefins which are used in the process as well as requiring a high percentage of selectivity to the desired compound. These objections may be attained by utilizing the process of the present invention in which the reaction is effected in the presence of certain catalytic compositions of matter of the type hereinafter set forth in greater detail.

It is therefore an object of this invention to provide a process for the synthesis of tertiary amines.

A further object of this invention is to provide a process for the synthesis of tertiary amines whereby economical, attractive yields of the desired product are obtained.

In one aspect an embodiment of this invention resides in a process for the preparation of a tertiary amine which comprises reacting an aldehyde, hydrogen and a nitrogen-containing compound having the formula:

in which the R's are independently selected from the group consisting of hydrogen, alkyl, aryl, cycloalkyl, aralkyl, and arkaryl radicals in the presence of a rhodium- or ruthenium-containing catalyst at reaction conditions, and recovering the resulting tertiary amine.

A specific embodiment of this invention is found in the process for the preparation of tertiary amines which comprises reacting dodecanal, hydrogen and dimethylamine at a temperature in the range of from about 50° to about 350° C. and a pressure in the range of from about 10 to about 300 atmospheres in the presence of a catalyst comprising rhodium chloride, and recovering the resulting dodecyldimethylamine.

Other objects and embodiments will be found in the following further detailed description of the present invention.

As hereinbefore set forth the present invention is concerned with a process for the synthesis of tertiary amines. The desired compounds are prepared by reacting a halide, hydrogen and a nitrogen-containing compound in the presence of certain catalytic compositions of matter. The reaction conditions which are employed to produce the desired results will include temperatures in the range of from about 50° to about 350° C. and pressures in the range of from about 10 to about 300 atmospheres. In the preferred embodiment of the invention the pressures which are employed will be the autogeneous pressures resulting from the presence of hydrogen in the reaction mixture. However, it is also contemplated within the scope of this invention that the pressures resulting from the use of hydrogen will comprise only a partial operating pressure, the remainder being provided for by the introduction of carbon monoxide and/or a substantially inert gas such as nitrogen, helium, argon, etc., into the reaction vessel. In addition, other reaction conditions which are present during the synthesis of the tertiary amines will include mole ratios of the various components. For example, the aldehyde will be present in a mole ratio within the range of from about 1:1 to about 3:1 moles of aldehyde/mole of nitrogen-containing compound, the particular ratio which is employed being dependent upon the number of hydrogen atoms present which are available for alkylation.

Examples of aldehydes which may be employed as one of the components in the reaction mixture will comprise open chains compounds containing from 2 to about 30 carbon atoms such as ethanal (acetaldehyde), propanal (propionaldehyde), butanal (butyraldehyde), pentanal (valeraldehyde), hexanal (caproaldehyde), heptanal, octanal (caprylaldehyde), nonanal (pelargonaldehyde), decanal (capraldehyde), undecanal, dodecanal, tridecanal, tetradecanal, pentadecanal, hexadecanal, heptadecanal, octadecanal, nonadecanal, eicosanal, henicosanal, docosanal, tricosanal, tetracosanal, pentacosanal, hexacosanal, heptacosanal, octacosanal, nonacosanal, triacontanal, etc., as well as branched chain isomers thereof, benzaldehyde, etc.

The aforesaid olefinic compounds are reacted with a nitrogen-containing compound having the formula:

in which the R's are independently selected from the group consisting of hydrogen, alkyl, aryl, cycloalkyl, aralkyl, and alkaryl radicals. Specific examples of this nitrogen-containing compound which constitutes a second component of the reaction mixture will include ammonia, primary amines such as methylamine, ethylamine, n-propylamine, isopropylamine, n-butylamine, t-butylamine, n-pentylamine, sec-pentylamine, the isomeric hexylamines, heptylamines, octylamines, nonylamines, decylamines, undecylamines, dodecylamines, tridecylamines, tetradecylamines, etc., aniline, o-toluidine, m-toluidine, p-toluidine, o-xylidine, m-xylidine, p-xylidine, 2-ethylaniline, 3-ethylaniline, 4-ethylaniline, 2-propylaniline, 3-propylaniline, 4-propylaniline, cyclopentylamine, cyclohexylamine, cycloheptylamine, cyclooctylamine, etc., secondary amines such as dimethylamine, diethylamine, di-n-propylamine, diisopropylamine, di-n-butylamine, di-t-butylamine, di-n-pentylamine, di-sec-pentylamine, the isomeric dihexylamines, diheptylamines, dioctylamines, dinonylamines, didecylamines, diundecylamines, didodecylamines, ditridecylamines, ditetradecylamines, etc., dianiline, di-o-toluidine, di-m-toluidine, di-p-toluidine, di-o-xylidine, di-m-xylidine, di-p-xylidine, di-2-ethylaniline, di-3-ethylaniline, di-4-ethylaniline, di-2-propylaniline, di-3propylaniline, di-4propylaniline, dicyclopentylamine, dicyclohexylamine, dicycloheptylamine, dicyclooctylamine, etc. It is to be understood that the aforementioned olefinic compounds and nitrogen-containing compounds are only representative of the class of compounds which may be employed as reactants, and that the present invention is not necessarily limited thereto.

The reaction between the aforementioned aldehydes and nitrogen-containing compounds along with hydrogen is effected in the presence of certain catalytic compositions of matter, said compositions comprising rhodium- or ruthenium-containing compounds. In the preferred embodiment of the invention, the rhodium- or ruthenium-containing compounds will comprise the metals or the nitrates, aldehydes, halocarbonyls or carbonyl complexes. Specific examples of these compounds which are employed will include rhodium, rhodium nitrate, rhodium chloride, rhodium bromide, rhodium iodide, rhodium fluoride, chlorodicarbonylrhodium dimer. rhodium carbonyl, chlorobis(ethylene)rhodium dimer, ruthenium, ruthenium nitrate, ruthenium chloride, ruthenium bromide, ruthenium iodide, ruthenium fluoride, dichlorotricarbonylruthenium dimer, ruthenium carbonyl, etc.

The process of the present invention may be effected in any suitable manner and may comprise either a batch or continuous type of operation. When a batch type of operation is used, a quantity of the nitrogen-containing compound which acts as a catalyst for the process is placed in an appropriate pressure resistant apparatus such as an autoclave of the rotating, rocking, or mixing type. The aldehyde which is utilized as one of the starting components in the present process may be the result of a prior process involving the reaction of an olefinic compound, a nitrogen-containing compound, carbon monoxide and hydrogen, said aldehyde being a by-product of said process in which the principal product also comprises a tertiary amine. After placing the components of the reaction in the autoclave, it is then sealed and hydrogen is charged thereto until the desired operating pressure is reached. Alternatively, as hereinbefore discussed, as higher pressures are to be employed a portion of the pressure may be afforded by the introduction of carbon monoxide or a substantially inert gas into the reaction zone. After reaching the proper operating pressure, the apparatus is then heated to the desired operating temperature which may range from about 50° to 350° C. or more and the apparatus is maintained thereat for a predetermined residence time which may range from about 0.5 up to about 10 hours or more in duration. Upon completion of the desired residence time, heating is discontinued and the apparatus and contents thereof are allowed to return to room temperature. Upon reaching room temperature the pressure is discharged, the apparatus is opened and the reaction mixture is recovered therefrom. After separation from the catalyst, the reaction mixture may then be subjected to conventional means of separation whereby the desired tertiary amine is separated from unreacted starting materials and/or unwanted side reaction products which may have formed, and recovered.

It is also contemplated within the scope of this invention that the synthesis of tertiary amines may be accomplished by utilizing a continuous method of operation. When utilizing this type of operation, the aldehyde and the nitrogen-containing compound are continuously charged to a reaction zone which is maintained at the proper operating conditions of temperature and pressure and which contains a catalyst of the type hereinbefore set forth. In addition to the continuous charging of the reactants to the operating zone, hydrogen is also charged thereto. As hereinbefore set forth, if a higher operating pressure than that which is afforded by the presence of hydrogen is desired, carbon monoxide and/or an inert gas may also be charged to the reactor through a separate line or the gases may be admixed prior to entry into said reactor and the resulting mixture charged thereto in a single stream. Upon completion of the desired residence time in the reaction zone, the reactor effluent is continuously withdrawn and subjected to conventional means of separation, such as fractional distillation, whereby the desired tertiary amine is separated from unreacted starting materials and/or undesired side reaction products which may have been formed, and recovered, while the aforesaid unreacted starting materials may be recycled to the reaction zone to form a portion of the feed stock.

Some specific examples of the type of tertiary amines which may be prepared according to the process of this invention will include propyldimethylamine, butyldimethylamine, pentyldimethylamine, hexyldimethylamine, heptyldimethylamine, octyldimethylamine, decyldimethylamine, dodecyldimethylamine, tetradecyldimethylamine, pentadecyldimethylamine, octadecyldimethylamine, eicosyldimethylamine, docosyldimethylamine, propyldiethylamine, octyldiethylamine, nonyldiethylamine, undecyldiethylamine, pentwdecyldiethylamine, octadecyldiethylamine, tripropylamine, butyldipropylamine, hexyldipropylamine, nonyldipropylamine, nonyldipropylamine, decyldipropylamine, tridecyldipropylamine, heptadecyldipropylamine, eicosyldipropylamine, tribytylamine, pentyldibutylamine, octyldibutylamine, dicyldibutylamine, undecyldibutylamine, tetradecyldibutylamine, nonadecyldibutylamine, phenyldiethylamine, phenyldipropylamine, phenyldioctylamine, phenyldidecylamine, phenylditetradecylamine, phenyldioctadecylamine, phenyldidocosylamine, cyclohexyldipropylamine, cyclohexyldihexylamine, cyclohexyldidecylamine, cyclohexyldidodecylamine, propyldiphenylamine, hexyldiphenylamine, octyldiphenylamine, undecyldiphenylamine, tetradecyldiphhenylamine, propyldicyclohexylamine, hexyldicyclohexylamine, octyldicyclohexylaamine, undecyldicyclohexylamine, tetradecylidicydlohexylamine, octyldi(p-tolyl)amine, decyldi(p-tolyl)amine, etc. It is to be understood that the aforementioned tertiary amines are only representative of the class of compounds which may be prepared according to the process described herein, and that the present invention is not necessarily limited thereto.

The following examples are given to illustrate the process of the present invention. However, it is to be understood that these examples are given merely for purposes of illustration and that the present invention is not necessarily limited thereto.

EXAMPLE I

In this example 0.013 gram of a catalyst comprising rhodium chloride was placed in the glass liner of a rotating autoclave. In addition, 14.07 grams of dodecanal and 4 grams of dimethylamine were also placed in the autoclave. The autoclave was sealed and a 1:1 mixture of carbon monoxide and hydrogen was charged to the autoclave until 150 atmospheres of the blend gas had been added. The autoclave was then heated to a temperature of 150° C. and maintained thereat for a period of 3 hours. During this time the pressure in the autoclave rose from 239 to 245. At the end of the 3 hour period heating was discontinued and the autoclave was allowed to return to room temperature. Upon reaching room temperature, the excess pressure was discharged and the reaction mixture was recovered therefrom. Analysis of the product by means of gas liquid chromatography and elementary analysis showed that there had been a 100% conversion of the aldehydes with a 79.1 wt. % selectivity to dodecyldimethylamine along with 18.9 wt. % selectivity to dodecyl alcohol.

EXAMPLE II

In this example 0.014 gram of rhodium chloride, 14.04 grams of dodecanal and 4 grams of dimethylamine were placed in the glass liner of a rotating autoclave which was then sealed and 150 atmospheres of hydrogen was charged thereto. The autoclave was then heated to a temperature of 150° C. and maintained thereat for a period of 3 hours. During this period the pressure in the autoclave rose from 236 atmospheres to 239 atmospheres and then dropped to 236 atmospheres. At the end of the 3 hour period heating was discontinued and the autoclave was allowed to return to room temperature. The excess pressure was discharged the autoclave was opened and the reaction mixture was recovered therefrom. Gas liquid chromatography and elementary analyses showed that there had been a 62.1% conversion of the dodecanal with an 88.2 wt. % selectivity to dodecyldimethylamine.

EXAMPLE III

To illustrate the necessity for a catalyst of the type hereinbefore set forth in greater detail a run in which 13.94 grams of dodecanal and 4 grams of dimethylamine were placed in the glass liner of a rotating autoclave. The autoclave, after being sealed was pressured with a 1:1 mole ratio of carbon monoxide and hydrogen until 150 atmospheres had been charged. The autoclave was then heated to a temperature of 150° C. and maintained thereat for a period of 3 hours, the pressure during this time rising from 236 atmospheres to 250 atmospheres. At the end of the 3 hour period heating was discontinued and after the autoclave had returned to room temperature the excess pressure discharged. The autoclave was opened and the reaction mixture which was recovered therefrom was subjected to gas liquid chromotographic and elementary analyses. These analyses determined that there had been only a 27.3% conversion of the aldehydes with a maximum 75% selectivity to dodecyldimethylamine.

EXAMPLE IV

In an manner similar to that set forth in the above examples, a mixture comprising dimethylamine, octanal and a catalyst comprising chlorodicarbonylrhodium dimer may be placed in an autoclave which is sealed and hydrogen charged thereto until a initial operating pressure of 150 atmospheres is reached. Thereafter the autoclave may be heated to a temperature of about 150° C. and maintained at this temperature for a period of 4 hours at the end of which time heating may be discontinued and the autoclave allowed to return to room temperature. After returning to room temperature, the excess pressure may be discharged and the autoclave opened. The reaction mixture may then be subjected to gas liquid chromatographic and elementary analyses to determine the presence of the desired tertiary amine namely octyldimethylamine.

EXAMPLE V

In this example a mixture of aniline, butanal and a catalyst comprising chlorobis(ethylene)rhodium dimer may be placed in the glass liner of rotating autoclave which is sealed and hydrogen charged thereto until an initial operating pressure of 150 atmospheres may be reached. After heating the autoclave to a temperature of 150° C. for a period of 3 hours to complete the reaction, heating may be discontinued and the autoclave allowed to return to room temperature. After discharge of the excess pressure the autoclave may be opened and the reaction mixture subjected to analyses of the type hereinbefore set forth to determine the presence of the desired compound, dibutylanilne.

EXAMPLE VI

In this example a catalyst comprising ruthenium black and an aldehyde comprising dodecanal may be placed in the glass liner of a rotating autoclave. The autoclave is then sealed and ammonia and hydrogen may be placed in until an initial operating pressure of 250 atmospheres is reached. The autoclave may then be heated to a temperature of 150° C. and maintained thereat for a period of 3 hours at the end of which time heating is discontinued and the autoclave is allowed to return to room temperature. After release of the excess pressure the autoclave may be opened and the reaction mixture which is recovered therefrom may be subjected to gas liquid chromatographic analysis and elementary analysis is determined the presence of the tertiary amine comprising tridodecylamine.

EXAMPLE VII

In this example a mixture of dimethylamine and docosanal along with the catalyst comprising rhodium carbonyl may be placed in the glass liner of a rocking autoclave. The autoclave is sealed and a blend gas consisting of a 1:1 mole ratio of carbon monoxide and hydrogen may be charged to the autoclave until an initial operating pressure of 150 atmospheres is reached. Thereafter the autoclave is heated to a temperature of 150° C. and maintained thereat for a period of 3 hours. At the end of the 3 hour period heating may be discontinued and the autoclave allowed to return to room temperature. After discharge of the excess pressure the autoclave may be opened and the reaction mixture recovered therefrom. This mixture may then be subjected to gas liquid chromatographic and elementary analyses to determine the presence of docosyldimethylamine.

I claim as my invention:

1. A process for the preparation of a tertiary amine which comprises reacting an aldehyde, hydrogen and a nitrogen-containing compound having the formula:

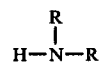

in which the R's are independently selected from the group consisting of hydrogen, alkyl, aryl, cycloalkyl, aralkyl, and alkaryl radicals in the presence of a catalyst selected from the group consisting of carbonyls and halocarbonyls of rhodium and ruthenium.

2. The process as set forth in claim 1 in which said reaction conditions include a temperature in the range of from about 50° to about 350° C. and a pressure in the range of from about 10 to about 300 atmospheres.

3. The process as set forth in claim 1 further characterized in that said process is also effected in the presence of carbon monoxide.

4. The process as set forth in claim 1 in which said catalyst is chlorodicarbonylrhodium dimer.

5. The process as set forth in claim 1 in which said catalyst is chlorobis(ethylene)rhodium dimer.

6. The process as set forth in claim 1 in which said catalyst is rhodium carbonyl.

7. The process as set forth in claim 1 in which said catalyst is ruthenium carbonyl.

8. The process as set forth in claim 1 in which said aldehyde is dodecanal, said nitrogen-containing compound is dimethylamine and said tertiary amine is dodecyldimethylamine.

9. The process as set forth in claim 1 in which said aldehyde is octanal, said nitrogen-containing compound is dimethylamine and said tertiary amine is octyldimethylamine.

10. The process as set forth in claim 1 in which said aldehyde is butanal, said nitrogen-containing compound is aniline, and said tertiary amine is dibutylaniline.

11. The process as set forth in claim 1 in which said aldehyde is dodecanal, said nitrogen-containing compound is ammonia and said tertiary amine is tridodecylamine.

12. The process as set forth in claim 1 in which said aldehyde is docosanal, said nitrogen-containing compound is dimethylamine and said tertiary amine is docosyldimethylamine.

* * * * *